(12) United States Patent
Ferraris et al.

(10) Patent No.: US 12,180,550 B2
(45) Date of Patent: Dec. 31, 2024

(54) GENE SIGNATURES FOR THE PREDICTION OF PROSTATE CANCER RECURRENCE

(71) Applicant: BRACCO IMAGING S.P.A., Milan (IT)

(72) Inventors: Andrea Ferraris, Genoa (IT); Erika Reitano, Banchette (IT); Alessandro Maiocchi, Monza (IT)

(73) Assignee: BRACCO IMAGING S.P.A., Milan (IT)

( * ) Notice: Subject to any disclaimer, the term of this patent is extended or adjusted under 35 U.S.C. 154(b) by 839 days.

(21) Appl. No.: 17/292,748

(22) PCT Filed: Nov. 8, 2019

(86) PCT No.: PCT/EP2019/080753
§ 371 (c)(1),
(2) Date: May 11, 2021

(87) PCT Pub. No.: WO2020/099277
PCT Pub. Date: May 22, 2020

(65) Prior Publication Data
US 2021/0395832 A1 Dec. 23, 2021

(30) Foreign Application Priority Data
Nov. 13, 2018 (EP) .................................. 18206054

(51) Int. Cl.
*C12Q 1/6886* (2018.01)
(52) U.S. Cl.
CPC ...... *C12Q 1/6886* (2013.01); *C12Q 2600/118* (2013.01); *C12Q 2600/158* (2013.01)
(58) Field of Classification Search
CPC ............ C12Q 1/6886; C12Q 2600/118; C12Q 2600/158
See application file for complete search history.

(56) References Cited

U.S. PATENT DOCUMENTS

2001/0053519 A1* 12/2001 Fodor ..................... G03F 7/265
536/24.1

FOREIGN PATENT DOCUMENTS

| WO | 2008121132 A2 | 10/2008 |
| WO | 2010056993 A2 | 5/2010 |
| WO | 2012006447 A2 | 1/2012 |
| WO | 2013185779 A2 | 12/2013 |

OTHER PUBLICATIONS

GeneAnnot. Retrieved on Feb. 29, 2024 from the internet: https://genecards.weizmann.ac.il/geneannot/index.shtml. (Year: 2024).*
"Affymetrix GeneChip Human Genome U133 Array Set HG-U133A," Gene Expression Omnibus (GEO) depository, available at https://www.ncbi.nlm.nih.gov/geo/query/acc.cgi?acc=GPL96 (2002).
Barrett, T, et al. "NCBI GEO: mining tens of millions of expression profiles—database and tools update," Nucleic Acids Res., 35:D760-D765 (2007).
Bettuzzi, S, et al. "Successful prediction of prostate cancer recurrence by gene profiling in combination with clinical data: a 5-year follow-up study," Cancer Res. 63(13):3469-72 (2003).
Bismar, TA, et al. "Defining aggressive prostate cancer using a 12-gene model," Neoplasia, 8:59-68 (2006).
Carroll, P, et al. "Prostate Cancer Early Detection, version 2.2015," Journal of the National Comprehensive Cancer Network, 13(12):1534-1561 (2015).
Chen, X, et al. "An Accurate Prostate Cancer Prognosticator Using a Seven-Gene Signature Plus Gleason Score and Taking Cell Type Heterogeneity into Account," PLoS One, 7(9): e45178 (2012).
Glinsky, GV et al. "Gene expression profiling predicts clinical outcome of prostate cancer," J Clin Invest., 113 (6):913-23 (2004).
International Search Report and Written Opinion for PCT/EP2019/080753, mailed Mar. 2, 2020.
Komisarof, J, et al. "A four gene signature predictive of recurrent prostate cancer," Oncotarget, 8(2):3430-3440 (2017).
Stephenson, AJ, et al. "Integration of gene expression profiling and clinical variables to predict prostate carcinoma recurrence after radical prostatectomy," Cancer, 104:290-298 (2005).
Sun, Y, et al. "Optimizing molecular signatures for predicting prostate cancer recurrence," Prostate, 69(10):1119-27 (2009).
Ward, JF, et al. "The long-term clinical impact of biochemical recurrence prostate cancer 5 or more years after radical prostatectomy," J Urol., 170:1872-1876 (2003).
Wold, S., et al. "PLS-Regression: A Basic Tool of Chemometrics," Chemometrics and Intelligent Laboratory Systems, 58, 109-130 (2001).

* cited by examiner

*Primary Examiner* — Joseph G. Dauner
(74) *Attorney, Agent, or Firm* — VIVICAR Law, PLLC (57) ABSTRACT

Disclosed are gene signatures and methods for predicting the recurrence of prostate cancer in prostatectomized subjects. Other objectives of the invention are assay devices and kits for determining the expression levels of specific gene sets correlated to prostate cancer recurrence.

11 Claims, 4 Drawing Sheets

GENE SIGNATURES FOR THE PREDICTION OF PROSTATE CANCER RECURRENCE

CROSS-REFERENCE TO RELATED APPLICATIONS

This application is the national stage application of corresponding international application number PCT/EP2019/080753, filed Nov. 8, 2019, which claims priority to and the benefit of European application no. 18206054.1, filed Nov. 13, 2018, which is hereby incorporated by reference in its entirety.

The present invention relates generally to the field of prostate cancer. More specifically the invention provides gene signatures and methods for predicting the recurrence of prostate cancer in prostatectomized subjects. Other objectives of the invention are assay devices and kits for determining the expression levels of specific gene sets correlated to prostate cancer recurrence.

BACKGROUND OF THE INVENTION

Prostate cancer (PCa) is the most common noncutaneous cancer and a leading cause of cancer-related deaths. Following primary curative treatment, PCa recurrence rates vary depending on stage, Gleason score (GS), and prostate-specific antigen (PSA) level. Although 20 to 30% of patients with clinically localized disease will relapse within 5 years after initial therapy, predicting an individual patient's risk of recurrence or metastatic progression remains challenging. It is difficult to predict recurrence and actual screening methods present technical limitations, patient discomfort and additional costs for the healthcare systems. Indeed, there is a need for new diagnostic methods enabling the stratification of patient population with higher risk of cancer recurrence after prostatectomy[1].

Of the patients who undergo prostatectomy for the treatment of clinically localized prostate carcinoma, 25-40% experience disease recurrence, manifested initially as an increasing level of prostate-specific antigen (PSA). An estimated 65% of these subjects develop clinical metastases within 10 years in the absence of salvage therapy. There is currently no evidence that patients who develop metastatic prostate carcinoma can be cured with existing systemic therapies. However, adjuvant systemic or local therapy after RP may potentially benefit patients at risk for metastatic disease progression.

Several criteria have been developed based on pathologic stage, tumor grade, and PSA level to predict cancer recurrence after prostatectomy but their prediction capabilities are uncertain.

Gene expression profiling of prostate carcinoma potentially offers an alternative tool to distinguish aggressive tumor biology and may improve the accuracy of outcome prediction for patients with prostate carcinoma treated by partial or radical prostatectomy.

Known Art

WO2013185779 concerns methods and tools for diagnosing prostate cancer and prognosing prostate cancer progression. The method comprises determining methylation level of the Clorf114, HAPLN3, AOX1, GAS6, ST6GALNAC3 and ZNF660 genes, which are used individually as independent markers of prostate cancer.

WO 2010056993 discloses methods for predicting the recurrence, progression, and metastatic potential of a prostate cancer in a subject, based on the detection of one or more gene biomarkers selected from FOXO1A, SOX9, CLNS1A, PTGDS, XPO1, LETMD1, RAD23B, ABCC3, APC, CHES1, EDNRA, FRZB, HSPG2, and TMPRSS2 ETV1 FUSION.

EP 2591126 relates to molecular markers and a diagnostic kit for the prognosis of different tumors, including prostate cancer. Also disclosed is a cell cycle progression signature of 31 genes, useful to estimate the risk of disease recurrence in post-prostatectomy patients.

WO2008121132 discloses a method for evaluating the presence of prostate cancer in a subject based on the quantitative determination of expression levels of different gene combinations.

Stephenson A. J. et al.[12] discloses a method for predicting prostate carcinoma recurrence after radical prostatectomy, which is based on a predictive model combining prognostic genes identified by molecular profiling with postoperative nomogram prediction. An association with recurrent carcinoma was identified for the GSTP1, GSTM1, EPB49, FAT, TGFB3 and ACPP genes.

Bettuzzi et al.[1] reports a study conducted on a cohort of prostate cancer patients undergoing radical prostatectomy. By means of a discriminant analysis they used a gene profile (alone or in combination with clinical/pathological data) for prognosis purpose.

Komisarof et al.[2] reports the identification of a gene signature differentially expressed in later recurred prostate cancer, and various predictive algorithms based on it.

Sun et al.[3] derived a 11-genes signature providing 87% overall accuracy for recurrence status prediction; they also identified a 5 genes subset that, when associated with clinical data, outperformed the previous genetic signature, providing an overall accuracy of 96%.

Chen et al.[4] identified a seven-genes classifier whose predictive ability in terms of accuracy, sensitivity and specificity were 69%, 76% and 59%, respectively.

Bismar et al.[5] selected 12 discriminant genes whose prediction performance were 57%, 96% and 0% as total accuracy, sensitivity and specificity, respectively.

Glinsky et al.[6] derived two 5-genes signatures, and one 4-genes signature whose performances ranged between 57% and 60% as accuracy, 56% and 100% as sensitivity and 0% and 59% as specificity.

Despite the several efforts to find a method able to predict the cancer recurrence with high accuracy and specificity, there is still a need for more reliable and efficient means for predicting with reasonable certainty the risk of coming back of a disease.

DESCRIPTION OF INVENTION

The present invention is based on the finding of new gene signatures (or gene panels: the two terms are herein used interchangeably) which allow to predict the recurrence of prostate cancer in a prostatectomized subject. According to the invention, the expression levels of genes from the identified gene signatures are determined in a sample from a prostatectomized subject and compared to the expression levels in reference samples. The inventors have found that the expression variability among genes in the identified gene signatures, compared to reference values, is predictive of an increased risk of recurrence of prostate cancer.

The minimum gene signature with tumor-recurrence prediction capability includes the following panel of genes: ACADVL, CARHSP1, CNTNAP1, DNASE1L2, RNF103, SEZ6L, SLC22A6, UGGT2, WDR52.

The predictive potential of this gene signature, e.g. in terms of discriminatory accuracy, can be increased by adding one or more of the following genes: ATP5D, C14orf109, CCDC144A, CDH15, CELSR3, DDX5, EHD4, EPHB3, LOC100508936, PABPC1, PIP4K2C, PLCG1

In a preferred embodiment, the gene signature is selected from the group consisting of:
(a) ACADVL, CARHSP1, CNTNAP1, DNASE1L2, RNF103, SEZ6L, SLC22A6, UGGT2, WDR52
(b) ACADVL, CARHSP1, CCDC144A, CNTNAP1, DDX5, DNASE1L2, EHD4, PIP4K2C, RNF103, SEZ6L, SLC22A6, UGGT2, WDR52;
(c) ACADVL, C14orf109, CARHSP1, CCDC144A, CDH15, CELSR3, CNTNAP1, DDX5, DNASE1L2, EHD4, PABPC1, PIP4K2C, RNF103, SEZ6L, SLC22A6, UGGT2, WDR52;
(d) ACADVL, ATPSD, C14orf109, CARHSP1, CCDC144A, CDH15, CELSR3, CNTNAP1, DDX5, DNASE1L2, EHD4, EPHB3, LOC100508936, PABPC1, PIP4K2C, PLCG1, RNF103, SEZ6L, SLC22A6, UGGT2, WDR52.

The discriminant power of the gene signatures of the invention results from the finding that the expression of the above genes is on average different in a subject (or a population of subjects) afflicted by a recurrence of PCa vis-à-vis a subject (or a population of subjects) not developing recurrence. From this average difference it is possible to obtain an expression profile map of two groups of differentially expressed genes.

In details, the genes on average over-expressed in subjects with recurrent PCa (or under-expressed in subjects with no recurrence PCa) are: C14orf109, CDH15, CELSR3, CNTNAP1, EHD4, EPHB3, PIP4K2C, RNF103, SLC22A6, UGGT2, WDR52.

The genes on average under-expressed in subjects with recurrent PCa (or over-expressed in subjects with no Pca recurrence) are: ACADVL, ATPSD, CARHSP1, DDX5, DNASE1L2, LOC100508936, PABPC1, PLCG1, SEZ6L.

The features of each gene of the gene signatures are described in the following Table I in terms of Gene Name and ENTREZ_GENE_ID.

TABLE I

| Gene Symbol* | Gene Name* | Entrez GeneID** |
|---|---|---|
| ACADVL | acyl-CoA dehydrogenase very long chain | 37 |
| ATP5D | ATP synthase, H+ transporting, mitochondrial F1 complex, delta subunit | 513 |
| C14orf109 | transmembrane protein 251 | 26175 |
| CARHSP1 | calcium regulated heat stable protein 1, 24 kDa | 23589 |
| CCDC144A | coiled-coil domain containing 144A | 9720 |
| CDH15 | cadherin 15, type 1, M-cadherin (myotubule) | 1013 |
| CELSR3 | cadherin, EGF LAG seven-pass G-type receptor 3 (flamingo homolog, *Drosophila*) | 1951 |
| CNTNAP1 | contactin associated protein 1 | 8506 |
| DDX5 | DEAD (Asp-Glu-Ala-Asp) box polypeptide 5 | 1655 |
| DNASE1L2 | deoxyribonuclease I-like 2 | 1775 |
| EHD4 | EH-domain containing 4 | 30844 |
| EPHB3 | EPH receptor B3 | 2049 |
| LOC100505870 | uncharacterized LOC100505870 | 100505870 |
| PABPC1 | poly(A) binding protein, cytoplasmic 1 | 26986 |
| PIP4K2C | phosphatidylinositol-5-phosphate 4-kinase, type II, gamma | 79837 |
| PLCG1 | phospholipase C, gamma 1 | 5335 |
| RNF103 | ring finger protein 103 | 7844 |
| SEZ6L | seizure related 6 homolog (mouse)-like | 23544 |
| SLC22A6 | solute carrier family 22 (organic anion transporter), member 6 | 9356 |
| UGGT2 | UDP-glucose glycoprotein glucosyltransferase 2 | 55757 |
| WDR52 | WD repeat domain 52 | 55779 |

*All genes symbols and names are according to the HUGO Gene Nomenclature Committee (http://www.genenames.org)

**All available information concerning the listed genes of Table I can be retrieved from the "Entrez Gene" portal (http://www.ncbi.nlm.nih.gov/gene) using the Entrez Gene ID provided in the table.

In one aspect, the invention provides a method of predicting the recurrence of a prostate cancer in a prostatectomized subject, the method comprising:
(1) determining, in a prostate tissue sample from said subject, the transcription expression levels of all the genes from the following gene panel: ACADVL, CARHSP1, CNTNAP1, DNASE1L2, RNF103, SEZ6L, SLC22A6, UGGT2, WDR52;
(2) determining the expression levels of the same genes in reference tissue samples, thereby providing an expression profile map for the recurrent and non-recurrent populations;
(3) subjecting the expression levels detected in the subject and those detected in the reference samples to an algorithm,
whereby the outcome of said algorithm is predictive of prostate cancer recurrence in said subject.

In one embodiment of the invention said gene panel further comprises one or more of the following genes: ATPSD, C14orf109, CCDC144A, CDH15, CELSR3, DDXS, EHD4, EPHB3, LOC100508936, PABPC1, PIP4K2C, PLCG1.

In a preferred embodiment said gene panel is selected from the group consisting of:
a) ACADVL, CARHSP1, CNTNAP1, DNASE1L2, RNF103, SEZ6L, SLC22A6, UGGT2, WDR52;
b) ACADVL, CARHSP1, CCDC144A, CNTNAP1, DDXS, DNASE1L2, EHD4, PIP4K2C, RNF103, SEZ6L, SLC22A6, UGGT2, WDR52;
c) ACADVL, C14orf109, CARHSP1, CCDC144A, CDH15, CELSR3, CNTNAP1, DDXS, DNASE1L2, EHD4, PABPC1, PIP4K2C, RNF103, SEZ6L, SLC22A6, UGGT2, WDR52; and
d) ACADVL, ATPSD, C14orf109, CARHSP1, CCDC144A, CDH15, CELSR3, CNTNAP1, DDXS, DNASE1L2, EHD4, EPHB3, LOC100508936, PABPC1, PIP4K2C, PLCG1, RNF103, SEZ6L, SLC22A6, UGGT2, WDR52.

It is a further object of the present invention a gene signature for predicting prostate cancer recurrence, wherein said gene signature is selected from the gene panels a), b), c) and d) defined above.

According to the method of invention, the subject has been previously treated with a surgical procedure for partial or complete removal of a prostate cancer and afterwards optionally subjected to treatments like radio- or chemotherapy or hormonal therapy. The tissue samples from the subject which are used for determining the expression levels of genes in the gene signature are taken from the surgically removed prostate.

As used herein, the term "subject" or "patient" refers to a human that can be afflicted by a prostate disease, including prostate cancer, and may or may not have such disease.

"Subject with risk of recurrence of prostate cancer" refers to a subject having one or more risk factors for developing prostate cancer, for instance depending on age, genetic predisposition, previous incidents with cancer and pre-existing non-cancer diseases.

"Prostate cancer recurrence" is intended as the condition where cancer comes back after a period of time in which it could not be detected. The recurrent prostate cancer might come back in the same place it first started (i.e. in the area of prostate gland, even when it is removed), in the lymph nodes near that place or somewhere else in the body. In either case it can be defined as recurrent prostate cancer.

"Predicting the risk of recurrence" of prostate cancer means that the subject to be analyzed by the method of the invention is allocated either into the group of subjects being at risk of recurrence or into the group of subjects being not at risk of recurrence. A subject at risk of recurrence of prostate cancer preferably has a risk of 90% or larger, or more preferably of 75% or larger, preferably within a predictive window of 5 years. A subject who is not at risk preferably has a risk lower than 20%, within 5 years.

"Gene signature" or "gene panel" means a combined group of genes with characteristic pattern of gene expression occurring as result of an altered or unaltered pathological medical condition, e.g. prostate cancer.

"Gene expression profile" or "gene expression pattern" refer to the measure of the activity (expression) of a set of genes at once, to create a global picture or map.

"Tissue sample" is a sample from a tissue or organ which may be obtained in particular from the prostate by, e.g., biopsy or resection, according to well known methods.

The "reference tissue samples" are likewise samples of prostate tissues taken from surgically removed prostate of previously-prostatectomized patients with known PCa outcome. They can be taken from prostatectomized patients with positive outcome, i.e. patients who have not developed metastatic processes in the prostate surgery follow-up (non-recurrent population), and patients with negative outcome, i.e. patients who have developed metastases after surgical removal of the prostate (recurrent population). Preferably the expression data of the reference samples are collected from groups of positive- and negative-outcome patients (non-recurrent and recurrent populations, respectively) of similar numerosity. The higher the number of reference samples, the more accurate the predictive potential of the gene signatures according to the invention. In one embodiment, the expression data from a significant number of prostatectomised patients with known prostate cancer outcome are used to set up a reference dataset and deriving an expression profile map, so providing a template for comparison to gene expression patterns generated from unknown prostate tissue samples. The use of the data of the expression profile map for predictive purpose may be realized by means of any suitable algorithm which properly combine and elaborate the expression levels detected in the test subject to predict cancer recurrence (as in Example 2).

In one embodiment the algorithm applied is a multivariate classification analysis method.

Preferably the multivariate analysis method is selected from Linear Discriminant Analysis (LDA), Partial Least Square Discriminant Analysis (PLS-DA) and K-Nearest Neighbors method (KNN).

In one embodiment the expression data are elaborated according to the following steps:
(a) providing the normalized gene expression level "z" as in equation below:

$$z = (x_{patient} - x_{reference})/S_{reference}$$

wherein $x_{patient}$ is the expression level for each gene from a gene panel in the sample from the subject, $x_{reference}$ is the expression level in the reference sample for the same gene and $S_{reference}$ is the standard deviation of the expression level across the reference sample
(b) calculating the sum of "z" for the under-expressed genes and for the over-expressed genes as defined above, thereby providing "$z_{under}$" and "$z_{over}$", respectively;
whereby:
if $z_{under}$ is higher than $z_{over}$, the prediction of prostate cancer recurrence is negative
if $z_{under}$ is lower than $z_{over}$, the prediction of prostate cancer recurrence is positive.

The transcription expression levels can be determined using methods and techniques known in the art and based on mRNA quantification. Suitable methods include quantitative PCR techniques, such as reverse transcription PCR (RT-PCR) or quantitative real-time RT-PCR, northern blot, RNA dot blot or tag based methods. Such methods are well known in the art, see e.g. Sambrook et al., Molecular Cloning: A Laboratory Manual, 4th Ed., Cold Spring Harbor Press, Cold Spring Harbor, N.Y., 2012.

The methods for quantitative mRNA detection are carried out by means of a suitable assay device comprising suitable supports and reagents, particularly sequence-specific polynucleotide probes immobilized on a support and capable of hybridizing with the mRNAs of the above-identified genes.

Preferably, the assay device is an array containing a solid support carrying multiple polynucleotide probes complementary and/or hybridizable to the gene transcripts. More preferably, the assay device is a microarray wherein the probes are immobilized on a solid glass substrate or membrane in separate locations or spots, whereby hybridization between the probes and the transcripts occur and the transcript amounts are measured by suitable colorimetric or radiometric measurements.

The array can comprise other elements that serve as controls or standards useful e.g. for the calibration of the signal readout.

In a further aspect, the invention provides a kit containing the assay device and reagents suitable for quantitative analysis of the above identified genes in a sample. Preferably said reagents are labeled primers or nucleotides (e.g. dNTPs) which are incorporated into the amplified sequence thereby allowing quantitative detection of the sample nucleic acid. In particular the kit may contain biotin labeled dNTPs and streptavidin linked reporter which are used in the amplification or transcription, or alternatively the kit nucleotides used in the amplification reaction or the amplified product can be labeled with different fluorescent or radioactive labelling groups. In addition, the kit may contain enzymes such as the reverse transcriptase. The assay device, reagents and enzymes are packed in suitable containers to allow their transport and storage.

In a yet further aspect, the invention provides the use of a gene signature, assay device or kit as herein defined for determining the risk of prostate cancer recurrence in a prostatectomized subject.

EXAMPLES

1. Dataset Used in this Study

The gene combinations for PCa recurrence prediction were tested on a gene expression profile (by microarray experiments) and clinical data set used in the study published by Stephenson et al.[1], containing 79 patients with clinically localized prostate cancer, treated by radical prostatectomy at MSKCC between 1993 and 1999 and classified by known disease recurrence status (40 non relapsed, 39 relapsed); no patient received any neo-adjuvant or adjuvant therapy before documented disease recurrence.

The genomic expression data, carried out using the Affymetrix U133A human gene array platform, were retrieved from the NCBI Gene Expression Omnibus[8] (GEO) database with accession code GSE2513 and used, as processed herein, for the computational analysis.

Originally, each patient was described by 22,283 features (probes expression) for individual gene/EST clusters; features with no associated genes were filtered out and the mean values were provided for probes mapping the same gene.

The resulting starting dataset was then composed by the 79 patients and 12,754 gene expressions values.

The gene combinations performances were assessed by a single evaluation set validation technique: for each investigated gene combination, the original dataset was randomly split into a training set (70% of the total samples) and a test set (30% of the total samples), both equally distributed between recurrent and not recurrent patients, then providing four different evaluation sets.

The classification models were then derived by means of the training reference samples and used to test the prediction performance for samples in the validation ones.

2. General Method

Upon the detection of the expression of the proposed genes, by genomic techniques, the $j^{th}$ gene signal level for the $i^{th}$ patient $(x_{i,j})$ is normalized across the reference samples by autoscaling procedure, providing new values $z_{i,j}$, as in equation below:

$$z_{i,j} = \frac{x_{i,j} - \bar{x}_{j\ ref}}{s_{j\ ref}} \qquad \text{Equation 1}$$

where: $\bar{x}_{j\ ref}$ and $s_{j\ ref}$ are the mean value and the standard deviation of the $j^{th}$ gene signal level across the reference samples.

Then, for each patient with outcome to be predicted the sum of the $z_1$ signals of the genes found under-expressed in recurrent status (i.e. ACADVL, ATP5D, CARHSP1, DDX5, DNASE1L2, LOC100508936, PABPC1, PLCG1, SEZ6L) and the sum of the $z_1$ signals of the genes found over-expressed in recurrent status (i.e. C14orf109, CDH15, CELSR3, CNTNAP1, EHD4, EPHB3, PIP4K2C, RNF103, SLC22A6, UGGT2, WDR52), are calculated, obtaining two scores, $Z_{Under}$ and $Z_{Over}$, respectively.

If $Z_{Under}$ is higher than $Z_{Over}$ the patient is predicted to not have recurrence; if $Z_{Under}$ is lower than $Z_{Over}$ the patient is predicted to have recurrence.

3. Predictive Capacity of a 21-Gene Signature

The means and standard deviations reference values, as in Equation 1, for the complete 21-gene signature were derived by the training set and detailed in Table II.

TABLE II

| | 21 genes mean ($\bar{x}_{ref}$) and standard deviation ($s_{ref}$) values of the reference patients. | | | | | | | | | | |
|---|---|---|---|---|---|---|---|---|---|---|---|
| | ACADVL | ATP5D | CARHSP1 | CCDC144A | DDX5 | DNASE1L2 | LOC 100508936 | PABPC1 | PLCG1 | SEZ6L | C14orf109 |
| $\bar{x}_{ref}$ | 336 | 582 | 2067 | 895 | 19 | 57 | 469 | 98 | 99 | 74 | 172 |
| $s_{ref}$ | 97 | 145 | 486 | 294 | 16 | 38 | 166 | 67 | 40 | 20 | 124 |

| | | CDH15 | CELSR3 | CNTNAP1 | EHD4 | EPHB3 | PIP4K2C | RNF103 | SLC22A6 | UGGT2 | WDR52 |
|---|---|---|---|---|---|---|---|---|---|---|---|
| | $\bar{x}_{ref}$ | 315 | 1050 | 89 | 170 | 233 | 138 | 74 | 196 | 287 | 50 |
| | $s_{ref}$ | 81 | 154 | 49 | 64 | 59 | 45 | 61 | 70 | 77 | 39 |

By solving the Equation 1 for the samples in the evaluation set the $z_{i,j}$ were derived as reported in Table III.

TABLE III 21 genes Z values of the patients in the evaluation set.

| | GSM617618 | GSM617651 | GSM617583 | GSM617593 | GSM617633 | GSM617619 | GSM617638 | GSM617621 | GSM617581 |
|---|---|---|---|---|---|---|---|---|---|
| Actual Recurrence | No | No | Yes | Yes | Yes | No | No | Yes | No |
| ACADVL | −0.8 | 0.7 | −0.3 | 0.6 | −0.4 | 0.2 | 0.7 | −0.3 | 2.4 |
| ATP5D | 0.3 | 0.0 | −0.9 | −1.0 | −0.2 | 1.1 | 4.4 | 0.0 | 0.6 |
| CARHSP1 | 0.2 | −0.6 | −1.1 | −1.2 | −1.1 | 0.4 | −0.3 | −1.0 | −0.3 |
| CCDC144A | 0.4 | 0.8 | −0.4 | −1.3 | −0.9 | −0.5 | −0.1 | −0.7 | −0.2 |
| DDX5 | 1.1 | −0.1 | −1.1 | −1.1 | −0.8 | 1.3 | 1.9 | −0.7 | −1.0 |
| DNASE1L2 | −0.8 | 0.1 | −0.8 | −1.3 | −1.3 | 0.6 | 0.3 | −0.3 | 0.1 |
| LOC100508936 | 1.3 | −0.7 | 0.9 | 0.3 | 0.2 | 0.2 | 0.2 | 0.2 | 0.6 |
| PABPC1 | −1.2 | −0.6 | −0.8 | −0.4 | −1.1 | 1.4 | 0.7 | −0.9 | −1.0 |
| PLCG1 | 0.7 | 1.9 | 0.0 | −0.6 | 0.0 | 1.8 | −0.6 | −1.2 | −0.3 |
| SEZ6L | −0.1 | −0.2 | −1.3 | −0.2 | 0.3 | −0.2 | 1.0 | 0.5 | 1.3 |
| C14orf109 | −0.4 | −0.8 | 1.5 | −0.6 | 0.0 | 0.4 | 0.2 | −0.2 | −0.1 |
| CDH15 | −0.4 | 0.2 | 1.6 | −0.4 | 0.4 | −0.7 | −2.2 | −1.2 | −0.7 |
| CELSR3 | 0.0 | −1.5 | −1.0 | 0.3 | −0.5 | 0.4 | 0.4 | 0.7 | 0.2 |
| CNTNAP1 | −1.2 | −1.1 | 0.9 | 0.2 | −0.8 | 1.7 | −1.0 | 0.4 | 1.0 |
| EHD4 | −0.1 | −1.3 | 0.6 | −0.2 | −0.7 | 0.7 | 1.1 | 0.9 | −1.3 |
| EPHB3 | −1.1 | −1.0 | −0.5 | 0.0 | −0.5 | 0.3 | 0.5 | 0.3 | −0.1 |
| PIP4K2C | −0.5 | 0.4 | −0.4 | 0.9 | 1.6 | −0.9 | −0.9 | 1.9 | −0.6 |
| RNF103 | −0.8 | 0.9 | 0.0 | 0.3 | 0.6 | −0.3 | −0.8 | −1.0 | −0.7 |
| SLC22A6 | −1.2 | 0.2 | 3.6 | −0.9 | −0.9 | −0.5 | 0.7 | −0.3 | −0.6 |
| UGGT2 | −0.6 | −1.0 | 0.8 | 0.5 | 3.6 | −0.9 | −0.8 | −1.4 | −1.5 |
| WDR52 | −0.8 | −0.9 | −0.3 | −0.4 | −0.9 | 0.8 | −0.8 | 0.6 | 1.3 |

| | GSM617657 | GSM617623 | GSM617628 | GSM617606 | GSM617656 | GSM617614 | GSM617634 | GSM617654 |
|---|---|---|---|---|---|---|---|---|
| Actual Recurrence | Yes | No | No | Yes | Yes | Yes | No | No |
| ACADVL | −1.3 | 4.5 | −0.8 | −0.7 | 0.6 | −1.4 | 0.5 | −0.1 |
| ATP5D | −1.2 | −1.4 | 0.6 | −1.3 | −0.3 | 0.3 | −0.3 | −0.4 |
| CARHSP1 | 0.7 | −1.0 | 0.6 | 0.7 | −1.5 | −0.8 | −1.0 | −0.8 |
| CCDC144A | 0.3 | −0.6 | 2.8 | −0.3 | −0.2 | 0.5 | −0.1 | 0.4 |
| DDX5 | −0.7 | 0.5 | −1.0 | 0.3 | −0.2 | −1.0 | 1.1 | 0.3 |
| DNASE1L2 | −0.1 | −0.3 | 0.1 | 0.0 | −0.4 | −0.9 | 0.2 | 0.9 |
| LOC100508936 | −1.7 | 1.0 | 0.5 | −0.9 | 0.7 | 0.1 | −0.8 | −0.7 |
| PABPC1 | 0.0 | 0.7 | 0.0 | −1.0 | −1.0 | −0.6 | 0.6 | −0.8 |
| PLCG1 | −1.0 | −0.8 | 0.9 | 1.1 | −0.5 | −0.2 | −0.1 | −1.3 |
| SEZ6L | −2.0 | 0.6 | 0.2 | −0.9 | −0.3 | −1.0 | 0.0 | 4.1 |
| C14orf109 | −1.2 | 0.3 | −0.3 | −1.1 | 0.4 | 0.5 | −0.5 | 1.4 |
| CDH15 | 0.8 | −0.4 | 1.1 | 0.2 | 0.2 | 0.3 | 0.0 | −0.4 |
| CELSR3 | 2.3 | −1.0 | −0.6 | 1.6 | −0.1 | 0.5 | −0.8 | −0.1 |
| CNTNAP1 | −1.4 | −0.7 | −0.5 | −0.9 | 1.6 | −0.8 | −1.3 | −0.8 |
| EHD4 | −0.6 | 0.0 | −0.9 | −0.5 | 0.5 | 1.3 | 0.7 | 0.8 |
| EPHB3 | −0.4 | −1.2 | 0.5 | −0.3 | −0.5 | 0.7 | −0.9 | −0.5 |
| PIP4K2C | −1.4 | −1.3 | −0.3 | −0.3 | −0.3 | 0.5 | −0.9 | −0.5 |
| RNF103 | 1.1 | −0.6 | −0.2 | 0.3 | 0.4 | 0.1 | −0.6 | −0.5 |
| SLC22A6 | −2.3 | −1.0 | 0.0 | 3.1 | 0.9 | 1.5 | −0.3 | −0.7 |
| UGGT2 | 3.6 | −0.9 | −1.0 | −0.5 | 1.4 | −0.3 | 0.1 | 0.3 |
| WDR52 | −0.1 | −0.4 | −0.3 | −0.4 | 0.6 | −0.2 | −0.1 | 0.8 |

| | GSM617600 | GSM617610 | GSM617590 | GSM617586 | GSM617641 | GSM617646 | GSM617609 |
|---|---|---|---|---|---|---|---|
| Actual Recurrence | Yes | Yes | No | Yes | No | Yes | No |
| ACADVL | −0.8 | 0.8 | −0.3 | −0.2 | 0.2 | −0.2 | 0.4 |
| ATP5D | −0.2 | −0.9 | 2.7 | 0.4 | −0.8 | −1.4 | 2.0 |
| CARHSP1 | −0.3 | −0.4 | 0.7 | −1.7 | −0.6 | −0.5 | −0.3 |
| CCDC144A | −0.9 | −0.7 | −1.0 | 0.0 | −0.1 | −1.2 | 0.4 |
| DDX5 | −0.8 | −0.5 | −0.2 | 1.7 | −0.7 | −1.0 | 0.7 |
| DNASE1L2 | −0.8 | −0.8 | 2.9 | −0.9 | 1.9 | 0.1 | −0.4 |
| LOC100508936 | −0.3 | −0.6 | −1.8 | −0.7 | −1.1 | −0.3 | −0.2 |
| PABPC1 | 0.0 | −1.0 | 1.1 | −1.1 | 3.0 | −1.1 | 0.0 |
| PLCG1 | −0.6 | 0.5 | 1.0 | 1.0 | 0.3 | 1.1 | 0.7 |
| SEZ6L | −2.5 | 0.6 | −0.4 | 1.5 | 1.8 | −0.2 | 2.1 |
| C14orf109 | −0.8 | 0.6 | −0.2 | 2.3 | 0.3 | −0.5 | −0.1 |
| CDH15 | −0.5 | −0.9 | −0.5 | −0.9 | 0.2 | 0.4 | −1.3 |
| CELSR3 | 1.0 | −0.7 | 0.4 | 0.7 | −1.3 | −0.8 | −0.2 |
| CNTNAP1 | 1.6 | 1.9 | −0.6 | 0.9 | −1.0 | 1.5 | −0.6 |
| EHD4 | 0.4 | 0.4 | 0.1 | 0.6 | −0.2 | 0.1 | 1.5 |
| EPHB3 | −0.2 | 1.8 | 0.5 | −1.1 | 1.3 | 0.0 | −1.6 |

TABLE III-continued

| | 21 genes Z values of the patients in the evaluation set. | | | | | | | |
|---|---|---|---|---|---|---|---|---|
| PIP4K2C | −0.4 | −0.7 | −0.5 | 0.2 | 1.3 | 0.9 | 0.2 |
| RNF103 | −0.7 | −0.1 | −0.8 | −0.5 | −0.6 | −0.6 | −0.7 |
| SLC22A6 | −1.2 | −0.3 | 0.2 | 3.3 | −0.3 | −1.7 | −0.1 |
| UGGT2 | 1.6 | 1.8 | −0.5 | 0.2 | −1.4 | 0.1 | 0.5 |
| WDR52 | −0.3 | 0.7 | −0.8 | 0.7 | −0.6 | 1.3 | −1.0 |

Then, for each patient in the evaluation set the $Z_{Under}$ and the $Z_{Over}$ were calculated and the results are provided in Table IV.

TABLE IV 21 gene scores ($Z_{Under}$ and $Z_{Over}$) of the patients in the evaluation set.

| Primary ID | GSM617618 | GSM617651 | GSM617583 | GSN1617593 | GSM617633 | GSM617619 | GSY1617638 | GSM617621 | GSM617581 |
|---|---|---|---|---|---|---|---|---|---|
| $Z_{Under}$ | 1.1 | 1.5 | −5.8 | −6.3 | −5.2 | 6.3 | 8.2 | −4.6 | 2.3 |
| $Z_{Over}$ | −7.0 | −6.0 | 6.8 | −0.3 | 1.9 | 1.0 | −3.7 | 0.6 | −3.2 |
| Actual Recurrence | No | No | Yes | Yes | Yes | No | No | Yes | No |
| Predicted Recurrence | No | No | Yes | Yes | Yes | No | No | Yes | No |

| Primary ID | GSM617657 | GSM617623 | GSM617628 | GSM617606 | GSM617656 | GSM617614 | GSM617634 | GSM617654 |
|---|---|---|---|---|---|---|---|---|
| $Z_{Under}$ | −6.9 | 3.1 | 3.8 | −2.9 | −3.2 | −5.1 | 0.2 | 1.5 |
| $Z_{Over}$ | 0.4 | −7.2 | −2.5 | 1.3 | 5.0 | 4.2 | −4.7 | −0.2 |
| Actual Recurrence | Yes | No | No | Yes | Yes | Yes | No | No |
| Predicted Recurrence | Yes | No | No | Yes | Yes | Yes | No | No |

| Primary ID | GSM617600 | GSM617610 | GSM617590 | GSM617586 | GSM617641 | GSM617646 | GSM617609 |
|---|---|---|---|---|---|---|---|
| $Z_{Under}$ | −7.3 | −3.0 | 4.7 | −0.1 | 4.1 | −4.7 | 5.5 |
| $Z_{Over}$ | 0.5 | 4.6 | −2.6 | 6.3 | −2.2 | 0.6 | −3.4 |
| Actual Recurrence | Yes | Yes | No | Yes | No | Yes | No |
| Predicted Recurrence | Yes | Yes | No | Yes | No | Yes | No |

The resulting overall accuracy in the evaluation set of the 21-gene classifier was 100%.

4. Predictive Capacity of a 17-Gene Signature

Means and standard deviations reference values, as in Equation 1, for a 17-gene combination were derived by the training set and detailed in Table V.

TABLE V 17 genes mean ($\bar{x}_{ref}$) and standard deviation ($s_{ref}$) values of the reference patients.

| | ACADVL | CARHSP1 | CCDC144A | DDX5 | DNASE1L2 | PABPC1 | SEZ6L | C14orf109 | CDH15 |
|---|---|---|---|---|---|---|---|---|---|
| $\bar{x}_{ref}$ | 341 | 2025 | 900 | 18 | 52 | 99 | 75 | 161 | 320 |
| $s_{ref}$ | 117 | 408 | 279 | 16 | 35 | 67 | 19 | 96 | 78 |

| | CELSR3 | CNTNAP1 | EHD4 | PIP4K2C | RNF103 | SLC22A6 | UGGT2 | WDR52 |
|---|---|---|---|---|---|---|---|---|
| $\bar{x}_{ref}$ | 1046 | 87 | 168 | 134 | 71 | 196 | 286 | 47 |
| $s_{ref}$ | 160 | 50 | 65 | 43 | 58 | 77 | 91 | 39 |

By solving the Equation 1 for the samples in the evaluation set the $z_{i,j}$ were derived as reported in Table VI.

TABLE VI 17 genes Z values of the patients in the evaluation set.

|  | GSM617607 | GSM617632 | GSM617596 | GSM617659 | GSM617622 | GSM617613 | GSM617626 | GSM617640 | GSM617589 |
|---|---|---|---|---|---|---|---|---|---|
| Actual Recurrence | No | No | Yes | Yes | No | Yes | No | No | Yes |
| ACADVL | 0.7 | −0.2 | −0.2 | −0.4 | 0.9 | 0.5 | 0.4 | 1.2 | −0.7 |
| CARHSP1 | 2.0 | 0.0 | 0.5 | −2.3 | 1.3 | −0.9 | −0.4 | 1.4 | −1.8 |
| CCDC144A | 0.0 | −0.5 | −1.2 | −0.8 | 1.4 | 0.1 | 0.2 | −0.1 | −0.6 |
| DDX5 | 2.2 | 0.6 | −1.0 | −0.9 | 1.5 | 1.4 | −0.7 | −0.2 | 1.3 |
| DNASE1L2 | −0.2 | 0.3 | −0.7 | −0.3 | 0.8 | 0.4 | 1.7 | −0.1 | 2.3 |
| PABPC1 | 0.9 | −1.1 | −0.5 | −1.1 | −1.0 | −0.1 | 1.1 | −0.2 | −0.6 |
| SEZ6L | −1.4 | −0.1 | −0.6 | −1.9 | 0.1 | −0.8 | 1.0 | −0.6 | −0.5 |
| C14orf109 | −1.2 | −0.3 | −0.3 | −0.2 | −0.9 | 6.0 | −0.6 | 0.4 | 2.3 |
| CDH15 | −1.3 | −0.9 | 0.7 | −0.6 | −1.0 | −1.4 | −0.9 | −1.7 | 1.5 |
| CELSR3 | 0.2 | −0.7 | 0.6 | 0.4 | −0.7 | 0.4 | 0.0 | 1.0 | 0.2 |
| CNTNAP1 | −0.9 | 0.0 | 0.7 | 0.2 | 0.8 | 2.6 | 0.4 | −1.3 | −0.3 |
| EHD4 | 0.7 | 1.3 | −0.4 | −0.4 | 0.3 | −0.8 | −0.6 | −0.2 | 1.5 |
| PIP4K2C | 0.4 | −1.9 | 1.1 | 1.1 | −0.9 | 0.3 | −0.1 | 1.3 | 1.4 |
| RNF103 | 0.4 | −0.7 | −0.2 | −0.3 | −0.8 | 2.1 | 0.6 | −0.8 | −0.4 |
| SLC22A6 | −0.8 | 0.1 | −0.5 | 0.0 | −1.4 | 2.8 | −0.8 | 0.0 | 0.1 |
| UGGT2 | 0.1 | −1.5 | 1.2 | −0.6 | 0.4 | 1.2 | −1.0 | −0.6 | 0.2 |
| WDR52 | −0.7 | 0.8 | −0.6 | −0.4 | −0.9 | −0.1 | 0.4 | −0.1 | −0.9 |

|  | GSM617642 | GSM617645 | GSM617625 | GSM617655 | GSM617648 | GSM617631 | GSM617634 | GSM617654 |
|---|---|---|---|---|---|---|---|---|
| Actual Recurrence | Yes | Yes | No | Yes | No | Yes | No | No |
| ACADVL | −0.6 | 0.4 | −0.9 | −0.6 | −0.1 | −0.7 | 0.4 | −0.2 |
| CARHSP1 | −1.9 | 3.1 | −0.6 | −1.4 | 1.7 | −1.0 | −1.1 | −0.8 |
| CCDC144A | −0.5 | 0.5 | −0.7 | −1.4 | 3.3 | −1.4 | −0.1 | 0.4 |
| DDX5 | −0.5 | −0.9 | 0.2 | 0.5 | 0.5 | 0.0 | 1.2 | 0.4 |
| DNASE1L2 | −0.6 | 0.8 | 0.4 | −1.1 | 1.6 | −0.7 | 0.4 | 1.2 |
| PABPC1 | −1.2 | −0.9 | −1.3 | −1.2 | 0.5 | −0.8 | 0.6 | −0.9 |
| SEZ6L | −0.9 | −1.1 | −0.3 | −1.3 | 2.2 | −1.6 | 0.0 | 4.3 |
| C14orf109 | −0.5 | 0.3 | −0.1 | 0.7 | −0.2 | 1.0 | −0.6 | 2.0 |
| CDH15 | 0.2 | −1.2 | −0.7 | 1.7 | 0.1 | −0.2 | 0.0 | −0.5 |
| CELSR3 | 1.5 | 1.1 | 0.1 | −1.6 | 0.4 | 0.3 | −0.8 | −0.1 |
| CNTNAP1 | 1.0 | −0.1 | −1.2 | 0.1 | −0.2 | −0.5 | −1.2 | −0.7 |
| EHD4 | 0.1 | 0.3 | −1.4 | 0.0 | 1.4 | −0.1 | 0.7 | 0.8 |
| PIP4K2C | 0.8 | −1.4 | −0.8 | −0.2 | 1.5 | 1.1 | −0.9 | −0.4 |
| RNF103 | −0.3 | 1.3 | 0.6 | −0.4 | −0.1 | 1.3 | −0.6 | −0.5 |
| SLC22A6 | 0.3 | 2.5 | −0.2 | 1.5 | −0.4 | −1.2 | −0.3 | −0.6 |
| UGGT2 | 1.4 | −0.4 | −0.4 | −0.6 | 0.5 | 1.4 | 0.1 | 0.2 |
| WDR52 | 0.1 | −0.8 | −0.4 | 0.1 | −0.9 | −0.8 | −0.2 | 0.8 |

|  | GSM617600 | GSM617610 | GSM617590 | GSM617586 | GSM617641 | GSM617646 | GSM617609 |
|---|---|---|---|---|---|---|---|
| Actual Recurrence | Yes | Yes | No | Yes | No | Yes | No |
| ACADVL | −0.7 | 0.6 | −0.3 | −0.2 | 0.1 | −0.2 | 0.3 |
| CARHSP1 | −0.3 | −0.4 | 1.0 | −1.9 | −0.6 | −0.5 | −0.2 |
| CCDC144A | −1.0 | −0.8 | −1.1 | 0.0 | −0.1 | −1.3 | 0.4 |
| DDX5 | −0.7 | −0.4 | −0.1 | 1.8 | −0.6 | −0.9 | 0.8 |
| DNASE1L2 | −0.7 | −0.7 | 3.3 | −0.9 | 2.2 | 0.2 | −0.2 |
| PABPC1 | −0.1 | −1.0 | 1.1 | −1.2 | 3.0 | −1.1 | 0.0 |
| SEZ6L | −2.8 | 0.6 | −0.5 | 1.5 | 1.9 | −0.3 | 2.2 |
| C14orf109 | −0.8 | 0.9 | −0.1 | 3.1 | 0.5 | −0.5 | 0.0 |
| CDH15 | −0.6 | −1.0 | −0.6 | −1.0 | 0.1 | 0.3 | −1.4 |
| CELSR3 | 1.0 | −0.6 | 0.4 | 0.7 | −1.2 | −0.7 | −0.2 |
| CNTNAP1 | 1.6 | 1.9 | −0.5 | 0.9 | −1.0 | 1.5 | −0.5 |
| EHD4 | 0.4 | 0.4 | 0.1 | 0.6 | −0.1 | 0.1 | 1.5 |
| PIP4K2C | −0.4 | −0.6 | −0.5 | 0.3 | 1.4 | 1.0 | 0.3 |
| RNF103 | −0.7 | −0.1 | −0.8 | −0.4 | −0.5 | −0.5 | −0.7 |
| SLC22A6 | −1.1 | −0.2 | 0.2 | 3.0 | −0.3 | −1.6 | −0.1 |
| UGGT2 | 1.4 | 1.5 | −0.4 | 0.2 | −1.2 | 0.1 | 0.4 |
| WDR52 | −0.3 | 0.7 | −0.8 | 0.7 | −0.6 | 1.2 | −1.0 |

Then, for each patient in the evaluation set the $Z_{Under}$ and the $Z_{Over}$ were calculated and the results are provided in Table VII (misclassified patients marked by an asterisk).

TABLE VII 17 gene scores ($Z_{Under}$ and $Z_{Over}$) of the patients in the evaluation set.

| Primary ID | GSM617607 | GSM617632 | GSM617596 | GSM617659 | GSM617622 | GSM617613 | GSM617626 | GSM617640 | GSM617589 |
|---|---|---|---|---|---|---|---|---|---|
| $Z_{Under}$ | 4.2 | −1.0 | −3.8 | −7.6 | 5.0 | 0.7 | 3.3 | 1.4 | −0.6 |
| $Z_{Over}$ | −3.0 | −3.7 | 2.4 | −0.8 | −5.0 | 13.0 | −2.5 | −2.1 | 5.5 |
| Actual Recurrence | No | No | Yes | Yes | No | Yes | No | No | Yes |
| Predicted Recurrence | No | No | Yes | Yes | No | Yes | No | No | Yes |

| Primary ID | GSM617642 | GSM617645 * | GSM617625 | GSM617655 | GSM617648 | GSM617631 | GSM617634 | GSM617654 |
|---|---|---|---|---|---|---|---|---|
| $Z_{Under}$ | −6.1 | 1.9 | −3.3 | −6.5 | 9.8 | −6.2 | 1.3 | 4.4 |
| $Z_{Over}$ | 4.6 | 1.5 | −4.5 | 1.3 | 2.1 | 2.4 | −3.7 | 1.0 |
| Actual Recurrence | Yes | Yes | No | Yes | No | Yes | No | No |
| Predicted Recurrence | Yes | No | No | Yes | No | Yes | No | No |

| Primary ID | GSM617600 | GSM617610 | GSM617590 | GSM617586 | GSM617641 | GSM617646 | GSM617609 |
|---|---|---|---|---|---|---|---|
| $Z_{Under}$ | −6.2 | −2.1 | 3.3 | −0.8 | 6.0 | −4.1 | 3.2 |
| $Z_{Over}$ | 0.4 | 2.9 | −2.9 | 8.0 | −2.8 | 0.8 | −1.7 |
| Actual Recurrence | Yes | Yes | No | Yes | No | Yes | No |
| Predicted Recurrence | Yes | Yes | No | Yes | No | Yes | No |

The resulting overall accuracy in the evaluation set of the 17-genes classifier was 96%, along with the associated statistics as reported in Table VIII.

TABLE VIII 17-gene signature general method classification performance. PPV and NPV statistics are estimated considering a disease (tumor recurrence) prevalence of 33% [9, 10].

|  | Value (%) |
|---|---|
| Sensitivity | 92 |
| Specificity | 100 |
| PPV | 100 |
| NPV | 92 |

5. Predictive Capacity of a 13-Gene Signature

Means and standard deviations reference values, as in Equation 1, for a 13-gene combination were derived by the training set and detailed in Table IX.

TABLE IX 13 genes mean ($\bar{x}_{ref}$) and standard deviation ($s_{ref}$) values of the reference patients.

|  | ACADVL | CARHSP1 | CCDC144A | DDX5 | DNASE1L2 | SEZ6L |
|---|---|---|---|---|---|---|
| $\bar{x}_{ref}$ | 332 | 1967 | 864 | 21 | 58 | 75 |
| $s_{ref}$ | 84 | 460 | 242 | 16 | 36 | 23 |

|  | CNTNAP1 | EHD4 | PIP4K2C | RNF103 | SLC22A6 | UGGT2 | WDR52 |
|---|---|---|---|---|---|---|---|
| $\bar{x}_{ref}$ | 91 | 172 | 138 | 71 | 193 | 292 | 46 |
| $s_{ref}$ | 52 | 65 | 42 | 60 | 83 | 93 | 37 |

By applying equation 1 to the samples in the evaluation set the $z_{i,j}$ were derived as detailed in Table X.

TABLE X 13 genes Z values of the patients in the evaluation set.

|  | GSM617592 | GSM617617 | GSM617653 | GSM617587 | GSM617591 | GSM617601 | GSM617605 | GSM617658 | GSM617582 |
|---|---|---|---|---|---|---|---|---|---|
| Actual Recurrence | No | No | No | Yes | Yes | Yes | Yes | Yes | No |
| ACADVL | 3.7 | 2.4 | 2.4 | −0.6 | −0.3 | −0.3 | −0.8 | −1.2 | −0.8 |
| CARHSP1 | 0.0 | 2.1 | −0.5 | 0.1 | 1.0 | −1.1 | 0.3 | −0.2 | 1.2 |
| CCDC144A | 0.6 | −0.2 | −0.6 | −1.3 | −0.9 | 1.0 | 1.9 | −1.0 | 0.7 |
| DDX5 | −0.9 | 1.1 | −1.2 | −1.0 | −0.9 | −1.0 | −0.9 | −0.7 | −1.0 |
| DNASE1L2 | 2.6 | −0.9 | −1.5 | −1.3 | 1.1 | 0.3 | 0.6 | −1.5 | 1.0 |
| SEZ6L | 1.4 | 0.6 | 0.5 | 0.6 | 0.4 | −1.4 | −0.5 | −1.1 | −1.2 |
| CNTNAP1 | −0.7 | −0.9 | −0.1 | 0.2 | −1.0 | 0.3 | −0.3 | −0.2 | 1.9 |
| EHD4 | −0.3 | −0.6 | −0.6 | 0.0 | 0.0 | 1.3 | 0.4 | 0.2 | −0.6 |
| PIP4K2C | −0.9 | −0.7 | −1.1 | 2.0 | −0.7 | −0.4 | −0.5 | 2.0 | −0.8 |
| RNF103 | 1.2 | −0.2 | 0.7 | −0.8 | 0.9 | −0.5 | −0.7 | 0.1 | −0.8 |
| SLC22A6 | −0.2 | 0.2 | 0.5 | 1.6 | 2.0 | −0.1 | 0.2 | −0.2 | −0.8 |
| UGGT2 | 0.1 | −0.2 | −1.0 | 0.8 | 0.8 | 0.8 | −0.4 | −1.1 | −0.2 |
| WDR52 | 1.0 | −1.0 | −1.0 | −0.9 | −0.8 | 0.5 | −0.8 | 0.0 | 1.0 |

|  | GSM617627 | GSM617629 | GSM617636 | GSM617616 | GSM617597 | GSM617623 | GSM617628 | GSM617606 |
|---|---|---|---|---|---|---|---|---|
| Actual Recurrence | No | Yes | No | No | Yes | No | No | Yes |
| ACADVL | 1.5 | −1.5 | −0.3 | 0.8 | 0.4 | 5.2 | −0.9 | −0.8 |
| CARHSP1 | 2.2 | −0.1 | 1.2 | 0.8 | −0.6 | −0.9 | 0.8 | 0.9 |
| CCDC144A | 2.3 | 0.8 | −1.1 | −0.7 | −0.9 | −0.6 | 3.6 | −0.2 |
| DDX5 | −1.0 | −0.8 | 0.7 | 1.3 | −1.2 | 0.4 | −1.1 | 0.2 |
| DNASE1L2 | −1.1 | −0.1 | −1.1 | −1.0 | −1.3 | −0.4 | 0.1 | 0.0 |
| SEZ6L | −0.6 | −1.2 | 0.6 | −0.1 | −1.7 | 0.4 | 0.1 | −0.9 |
| CNTNAP1 | −1.4 | 1.9 | −0.5 | −0.6 | 0.4 | −0.7 | −0.5 | −0.9 |
| EHD4 | 0.3 | −0.2 | −1.2 | −0.9 | 1.1 | 0.0 | −1.0 | −0.5 |
| PIP4K2C | −0.2 | −1.9 | −1.3 | −0.4 | −1.2 | −1.4 | −0.3 | −0.3 |
| RNF103 | −0.1 | 0.0 | −0.8 | 0.2 | −0.5 | −0.5 | −0.1 | 0.3 |
| SLC22A6 | −0.5 | 0.3 | 0.0 | −0.1 | 0.4 | −0.8 | 0.0 | 2.7 |
| UGGT2 | 0.4 | −0.9 | −1.1 | −0.4 | 1.4 | −0.8 | −0.9 | −0.5 |
| WDR52 | 0.2 | 0.9 | 1.8 | −1.0 | 0.1 | −0.4 | −0.4 | −0.5 |

|  | GSM617656 | GSM617614 | GSM617648 | GSM617631 | GSM617641 | GSM617646 | GSM617609 |
|---|---|---|---|---|---|---|---|
| Actual Recurrence | Yes | Yes | No | Yes | No | Yes | No |
| ACADVL | 0.7 | −1.5 | 0.0 | −0.9 | 0.3 | −0.2 | 0.5 |
| CARHSP1 | −1.4 | −0.7 | 1.7 | −0.8 | −0.4 | −0.3 | −0.1 |
| CCDC144A | −0.2 | 0.7 | 4.0 | −1.4 | 0.1 | −1.4 | 0.7 |
| DDX5 | −0.3 | −1.1 | 0.3 | −0.2 | −0.8 | −1.1 | 0.5 |
| DNASE1L2 | −0.5 | −1.0 | 1.5 | −0.9 | 2.0 | 0.0 | −0.4 |
| SEZ6L | −0.4 | −1.0 | 1.9 | −1.4 | 1.6 | −0.3 | 1.9 |
| CNTNAP1 | 1.5 | −0.8 | −0.3 | −0.5 | −1.0 | 1.4 | −0.6 |
| EHD4 | 0.5 | 1.2 | 1.4 | −0.2 | −0.2 | 0.0 | 1.4 |
| PIP4K2C | −0.4 | 0.5 | 1.4 | 1.1 | 1.4 | 1.0 | 0.2 |
| RNF103 | 0.5 | 0.2 | −0.1 | 1.3 | −0.5 | −0.5 | −0.7 |
| SLC22A6 | 0.8 | 1.3 | −0.3 | −1.0 | −0.2 | −1.4 | −0.1 |
| UGGT2 | 1.1 | −0.3 | 0.5 | 1.3 | −1.2 | 0.0 | 0.3 |
| WDR52 | 0.6 | −0.3 | −0.9 | −0.8 | −0.6 | 1.3 | −1.0 |

Then, for each patient in the evaluation set the $Z_{Under}$ and the $Z_{Over}$ were calculated and the results are provided in Table VII (misclassified patients marked by an asterisk).

TABLE XI 13 gene scores ($Z_{Under}$ and $Z_{Over}$) of the patients in the evaluation set.

| Primary ID | GSM617592 | GSM617617 | GSM617653 | GSM617587 | GSM617591 | GSM617601 | GCM617605 * | GSM617658 | GSM617582 |
|---|---|---|---|---|---|---|---|---|---|
| $Z_{Under}$ | 7.3 | 5.0 | −0.8 | −3.5 | 0.5 | −2.6 | 0.7 | −5.7 | −0.2 |
| $Z_{Over}$ | 0.3 | −3.5 | −2.6 | 2.9 | 1.2 | 2.0 | −2.1 | 0.8 | −0.3 |
| Actual Recurrence | No | No | No | Yes | Yes | Yes | Yes | Yes | No |
| Predicted Recurrence | No | No | No | Yes | Yes | Yes | No | Yes | No |

TABLE XI-continued 13 gene scores ($Z_{Under}$ and $Z_{Over}$) of the patients in the evaluation set.

| Primary ID | GSM617627 | GSM617629 | GSM617636 | GSM617616 | GSM617597 | GSM617623 | GSM617628 | GSM617606 |
|---|---|---|---|---|---|---|---|---|
| $Z_{Under}$ | 3.4 | -2.9 | 0.0 | 1.1 | -5.4 | 4.2 | 2.6 | -0.8 |
| $Z_{Over}$ | -1.4 | 0.2 | -3.0 | -3.3 | 1.6 | -4.6 | -3.1 | 0.4 |
| Actual Recurrence | No | Yes | No | No | Yes | No | No | Yes |
| Predicted Recurrence | No | Yes | No | No | Yes | No | No | Yes |

| Primary ID | GSM617656 | GSM617614 | GSM617648 | GSM617631 | GSM617641 | GSM617646 | GSM617609 |
|---|---|---|---|---|---|---|---|
| $Z_{Under}$ | -2.0 | -4.5 | 9.3 | -5.6 | 2.8 | -3.1 | 3.1 |
| $Z_{Over}$ | 4.5 | 2.0 | 1.7 | 1.1 | -2.3 | 1.8 | -0.3 |
| Actual Recurrence | Yes | Yes | No | Yes | No | Yes | No |
| Predicted Recurrence | Yes | Yes | No | Yes | No | Yes | No |

The resulting overall accuracy in the evaluation set of the 13-genes classifier was again 96%, along with the associated statistics as reported in Table XII.

TABLE XII 13-gene signature general method classification statistics. PPV and NPV Statistics are estimated considering a disease (tumor recurrence) prevalence of 33% [9, 10].

| | Value (%) |
|---|---|
| Sensitivity | 92 |
| Specificity | 100 |
| PPV | 100 |
| NPV | 92 |

6. Predictive Capacity of a 9-Gene Signature

Means and standard deviations reference values, as in Equation 1, for the core 9-gene combination were derived by the training set and detailed in Table XIII.

TABLE XIII 9 genes mean ($\bar{x}_{ref}$) and standard deviation ($s_{ref}$) values of the reference patients.

| | ACADVL | CARHSP1 | DNASE1L2 | SEZ6L | CNTNAP1 | RNF103 | SLC22A6 | UGGT2 | WDR52 |
|---|---|---|---|---|---|---|---|---|---|
| $\bar{x}_{ref}$ | 342.1 | 1994.9 | 56.5 | 76.5 | 95.9 | 67.9 | 191.9 | 293.5 | 43.9 |
| $s_{ref}$ | 108.7 | 411.7 | 34.5 | 22.1 | 54.0 | 56.2 | 79.0 | 84.9 | 36.9 |

By applying equation 1 to the samples in the evaluation set the $z_{i,j}$ were derived as detailed in Table XIV

TABLE XIV 9 genes Z values of the patients in the evaluation set.

| | GSM617639 | GSM617650 | GSM617595 | GSM617630 | GSM617620 | GSM617647 | GSM617602 | GSM617581 | GSM617657 |
|---|---|---|---|---|---|---|---|---|---|
| Actual Recurrence | No | No | Yes | Yes | No | No | Yes | No | Yes |
| ACADVL | 0.6 | -0.1 | -0.5 | 0.6 | 0.6 | 0.9 | -1.3 | 2.1 | -1.2 |
| CARHSP1 | -0.3 | -0.9 | -0.5 | 0.2 | 2.7 | 1.7 | -0.7 | -0.2 | 1.0 |
| DNASE1L2 | -0.2 | -0.6 | -1.3 | -0.4 | 2.3 | -0.2 | 0.6 | 0.1 | 0.0 |
| SEZ6L | 0.5 | -0.1 | 0.4 | 0.9 | -0.6 | 0.1 | -1.5 | 1.1 | -1.9 |
| CNTNAP1 | -1.3 | 0.0 | 0.4 | -1.0 | -0.6 | -0.3 | -1.2 | 0.7 | -1.4 |
| RNF103 | -0.6 | -0.6 | 1.0 | 2.4 | -0.5 | -0.7 | 0.6 | -0.6 | 1.3 |
| SLC22A6 | 0.9 | -0.6 | -0.4 | 1.6 | -0.7 | -0.2 | -0.4 | -0.5 | -2.0 |
| UGGT2 | -1.3 | -0.4 | 0.1 | -1.5 | 0.2 | -0.8 | 0.1 | -1.5 | 3.2 |
| WDR52 | -0.6 | -0.5 | 0.1 | 1.5 | -0.1 | -1.0 | 1.7 | 1.4 | 0.0 |

TABLE XIV-continued 9 genes Z values of the patients in the evaluation set.

|  | GSM617626 | GSM617640 | GSM617589 | GSM617642 | GSM617645 | GSM617625 | GSM617655 | GSM617590 |
| --- | --- | --- | --- | --- | --- | --- | --- | --- |
| Actual Recurrence | No | No | Yes | Yes | Yes | No | Yes | No |
| ACADVL | 0.4 | 1.3 | −0.7 | −0.7 | 0.5 | −1.0 | −0.7 | −0.4 |
| CARHSP1 | −0.3 | 1.4 | −1.8 | −1.8 | 3.1 | −0.6 | −1.3 | 1.1 |
| DNASE1L2 | 1.6 | −0.2 | 2.2 | −0.7 | 0.7 | 0.3 | −1.3 | 3.2 |
| SEZ6L | 0.7 | −0.6 | −0.5 | −0.8 | −1.0 | −0.4 | −1.1 | −0.5 |
| CNTNAP1 | 0.2 | −1.3 | −0.4 | 0.8 | −0.3 | −1.3 | −0.1 | −0.7 |
| RNF103 | 0.7 | −0.8 | −0.4 | −0.2 | 1.4 | 0.7 | −0.3 | −0.7 |
| SLC22A6 | −0.8 | 0.0 | 0.2 | 0.4 | 2.4 | −0.1 | 1.5 | 0.3 |
| UGGT2 | −1.1 | −0.8 | 0.1 | 1.4 | −0.6 | −0.5 | −0.7 | −0.5 |
| WDR52 | 0.5 | 0.0 | −0.9 | 0.2 | −0.8 | −0.3 | 0.2 | −0.8 |

|  | GSM617586 | GSM617636 | GSM617616 | GSM617597 | GSM617614 | GSM617631 | GSM617609 |
| --- | --- | --- | --- | --- | --- | --- | --- |
| Actual Recurrence | Yes | No | No | Yes | Yes | Yes | No |
| ACADVL | −0.2 | −0.3 | 0.5 | 0.2 | −1.3 | −0.8 | 0.3 |
| CARHSP1 | −1.8 | 1.3 | 0.8 | −0.8 | −0.8 | −0.9 | −0.2 |
| DNASE1L2 | −1.0 | −1.1 | −1.0 | −1.3 | −0.9 | −0.9 | −0.4 |
| SEZ6L | 1.2 | 0.6 | −0.1 | −1.7 | −1.0 | −1.4 | 1.8 |
| CNTNAP1 | 0.7 | −0.6 | −0.7 | 0.3 | −0.8 | −0.6 | −0.6 |
| RNF103 | −0.4 | −0.8 | 0.2 | −0.5 | 0.3 | 1.5 | −0.7 |
| SLC22A6 | 3.0 | 0.0 | −0.1 | 0.4 | 1.4 | −1.1 | −0.1 |
| UGGT2 | 0.1 | −1.2 | −0.4 | 1.5 | −0.3 | 1.4 | 0.3 |
| WDR52 | 0.8 | 1.9 | −1.0 | 0.1 | −0.2 | −0.7 | −1.0 |

Then, for each patient in the evaluation set the $Z_{Under}$ and the $Z_{Over}$ were calculated and the results are provided in Table XV (misclassified patients marked by an asterisk).

TABLE XV 9 gene scores ($Z_{Under}$ and $Z_{Over}$) of the patients in the evaluation set.

| Primary ID | GSM617639 | GSM617650 | GSM617595 | GSM617630 | GSM617620 | GSM617647 | GSM617602 | GSM617581 | GSM617657 |
| --- | --- | --- | --- | --- | --- | --- | --- | --- | --- |
| $Z_{Under}$ | 0.6 | −1.8 | −1.9 | 1.4 | 5.0 | 2.5 | −2.9 | 3.1 | −2.1 |
| $Z_{Over}$ | −2.8 | −2.2 | 1.2 | 2.9 | −1.7 | −3.1 | 0.8 | −0.4 | 1.1 |
| Actual Recurrence | No | No | Yes | Yes | No | No | Yes | No | Yes |
| Predicted Recurrence | No | No | Yes | Yes | No | No | Yes | No | Yes |

| Primary ID | GSM 617626 | GSM617640 | GSM617589 * | GSM617642 | GSM617645 * | GSM617625 | GSM617655 | GSM617590 |
| --- | --- | --- | --- | --- | --- | --- | --- | --- |
| $Z_{Under}$ | 2.5 | 1.9 | −0.8 | −4.0 | 3.3 | −1.6 | −4.4 | 3.4 |
| $Z_{Over}$ | −0.5 | −2.9 | −1.4 | 2.5 | 2.2 | −1.6 | 0.5 | −2.4 |
| Actual Recurrence | No | No | Yes | Yes | Yes | No | Yes | No |
| Predicted Recurrence | No | No | No | Yes | No | No | Yes | No |

| Primary ID | GSM617586 | GSM617636 | GSM617616 | GSM617597 | GSM617614 | GSM617631 | GSM617609 |
| --- | --- | --- | --- | --- | --- | --- | --- |
| $Z_{Under}$ | −1.8 | 0.4 | 0.2 | −3.6 | −4.0 | −4.0 | 1.5 |
| $Z_{Over}$ | 4.1 | −0.6 | −2.0 | 1.8 | 0.3 | 0.4 | −2.0 |
| Actual Recurrence | Yes | No | No | Yes | Yes | Yes | No |
| Predicted Recurrence | Yes | No | No | Yes | Yes | Yes | No |

The resulting overall accuracy in the evaluation set of the 9-genes classifier was 92%, along with the associated statistics as reported in Table XVI.

TABLE XVI 9-gene signature general method classification statistics. PPV and NPV statistics are estimated considering a disease (tumor recurrence) prevalence of 33% [9, 10].

|  | Value (%) |
| --- | --- |
| Sensitivity | 83 |
| Specificity | 100 |
| PPV | 100 |
| NPV | 86 |

7. Gene Signature Validation by Means of a Latent Variables Projection Based Classification Method.

The combinations of the genes for PCa recurrence prediction were tested by PLS Discriminant Analysis[11], a multivariate regression technique adopted for classification purposes.

7.1 Validation of the 21-Gene Signature

By selecting only the 21 gene expression values of the proposed signature from the entire dataset, a discriminant model with 1 component ($R^2=88\%$ and $Q^2=85\%$) was derived.

Taking as reference the recurrence status, the signs of the regression coefficients associated to each gene (Table XVII) reflected the over- or under-expression pattern in the recurrent states, as detailed in Table I.

TABLE XVII

Coefficients of the scaled and centered data of the 21-gene signature PLS-DA model.

| Gene Symbol | Coefficient |
| --- | --- |
| ACADVL | −0.15 |
| ATP5D | −0.11 |
| C14orf109 | 0.12 |
| CARHSP1 | −0.17 |
| CCDC144A | −0.12 |
| CDH15 | 0.12 |
| CELSR3 | 0.12 |
| CNTNAP1 | 0.15 |
| DDX5 | −0.12 |
| DNASE1L2 | −0.13 |
| EHD4 | 0.12 |
| EPHB3 | 0.10 |
| LOC100508936 | −0.12 |
| PABPC1 | −0.12 |
| PIP4K2C | 0.12 |
| PLCG1 | −0.10 |
| RNF103 | 0.14 |
| SEZ6L | −0.17 |
| SLC22A6 | 0.14 |
| UGGT2 | 0.13 |
| WDR52 | 0.13 |

Figure 1:
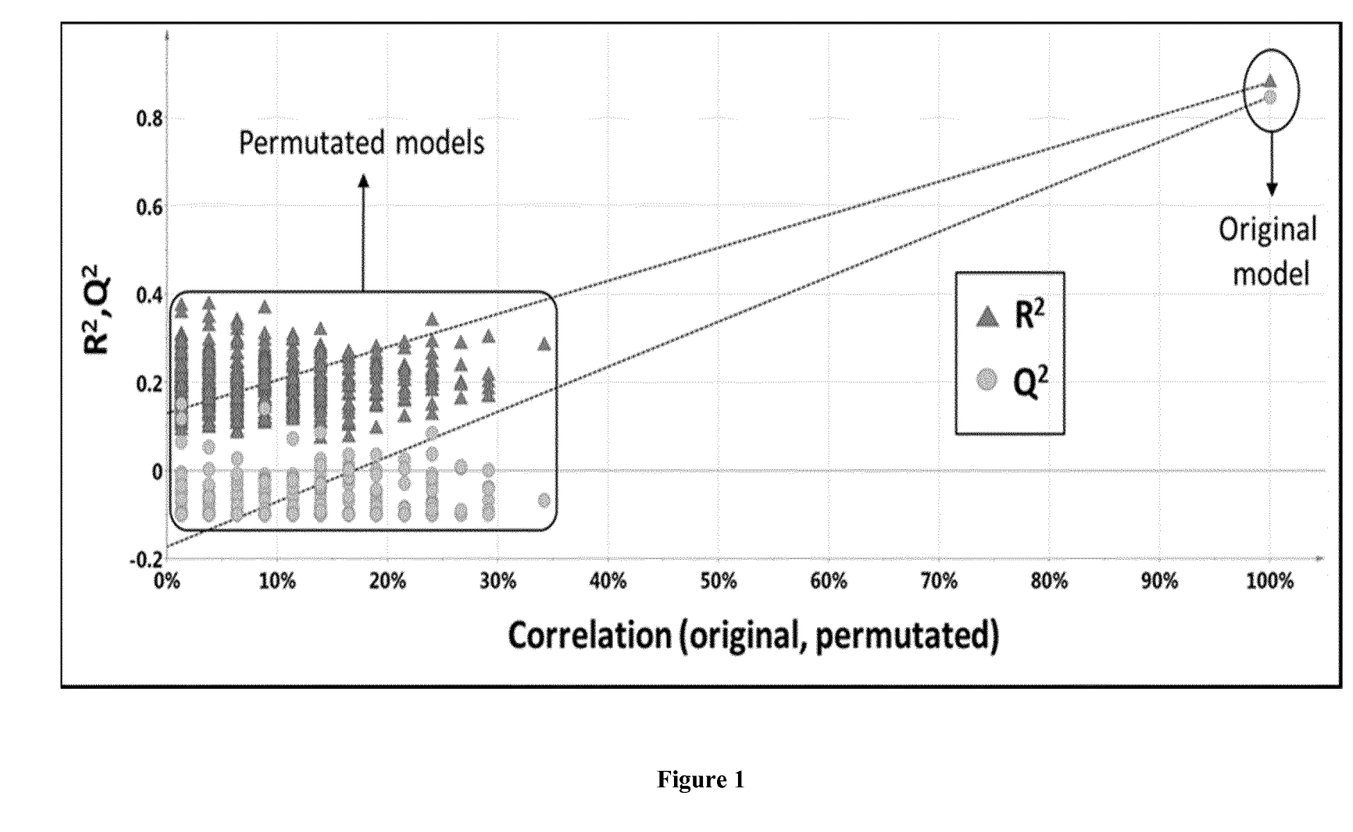
FIG. 1: Perturbation test results for the PLS-DA model of the 21-genes signature. X-axis shows the correlation coefficient (%) between the permutated and the original data. Y-axis is the value of $R^2$ and $Q^2$. The two values on the right hand corner correspond to the values of $R^2$ and $Q^2$ for the original model. Each value on the left side of the plot represents a permutation result. $R^2$ and $Q^2$ values are represented as dark gray triangles and light gray circles, respectively.

A preliminary validation of the 21-gene model was carried out via a Permutation test, in order to estimate the degree of overfitting of the model: the class assignment (recurrent and not recurrent) of the patients was randomly permuted 500 times, generating as much models for which $R^2$ and $Q^2$ values were calculated (FIG. 1).

By this calculation it was clear that it was not possible to obtain a model with the same goodness of fit and predictive properties simply by change.

According to the evaluation set, the resulting overall accuracy in classification of the 21-gene classifier was 100%.

7.2 Validation of the 17-Gene Signature

By selecting only the 17 gene expression values of the proposed signature from the entire dataset, a discriminant model with 1 component ($R^2=80\%$ and $Q^2=73\%$) was derived. Taking as reference the recurrence status, the signs of the regression coefficients associated to each gene (Table XVIII) reflected the over- or under-expression pattern in the recurrent states, as detailed in Table I.

TABLE XVIII

Coefficients of the scaled and centered data of the 17-gene signature PLS-DA model.

| Gene Symbol | Coefficient |
| --- | --- |
| ACADVL | −0.16 |
| C14orf109 | 0.12 |
| CARHSP1 | −0.20 |
| CCDC144A | −0.10 |
| CDH15 | 0.13 |
| CELSR3 | 0.13 |
| CNTNAP1 | 0.10 |
| DDX5 | −0.14 |
| DNASE1L2 | −0.11 |
| EHD4 | 0.20 |
| PABPC1 | −0.09 |
| PIP4K2C | 0.15 |
| RNF103 | 0.15 |
| SEZ6L | −0.16 |
| SLC22A6 | 0.14 |
| UGGT2 | 0.12 |
| WDR52 | 0.16 |

Figure 2:
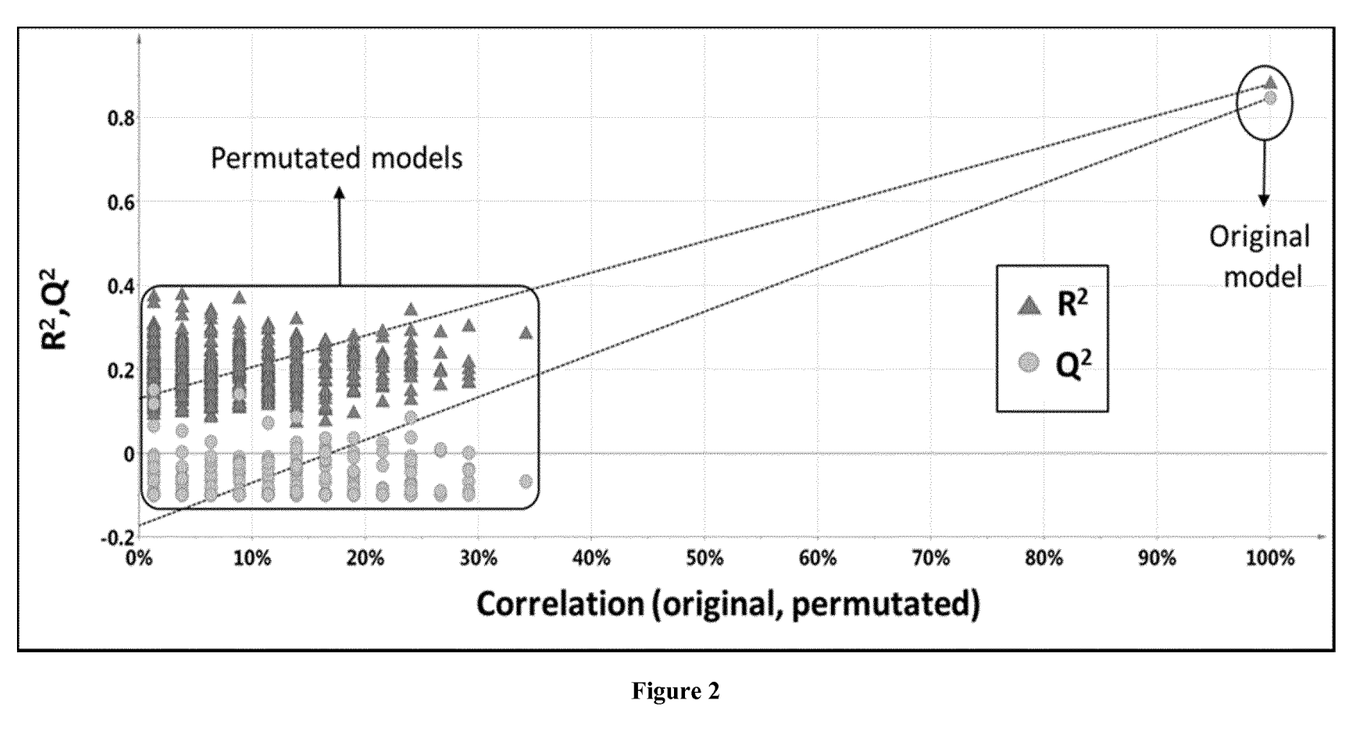
FIG. 2: Perturbation test results for the PLS-DA model of the 17-genes signature. X-axis shows the correlation coefficient (%) between the permutated and the original data. Y-axis is the value of $R^2$ and $Q^2$. The two values on the right hand corner correspond to the values of $R^2$ and $Q^2$ for the original model. Each value on the left side of the plot represents a permutation result. $R^2$ and $Q^2$ values are represented as dark gray triangles and light gray circles, respectively.

A preliminary validation of the 21-gene model was carried out via a Permutation test[5], in order to estimate the degree of overfitting of the model: the class assignment (recurrent and not recurrent) of the patients was randomly permuted 500 times, generating as much models for which $R^2$ and $Q^2$ values were calculated (FIG. 2).

By this calculation it was clear that it was not possible to obtain a model with the same goodness of fit and predictive properties simply by change.

According to the evaluation set, the resulting overall accuracy in classification of this 17-gene classifier was 96%, along with the associated statistics as reported in Table XIX.

TABLE XIX 17-gene signature PLS-DA classification statistics. PPV and NPV statistics are estimated considering a disease (tumor recurrence) prevalence of 33% [9, 10].

|  | Value (%) |
| --- | --- |
| Sensitivity | 92 |
| Specificity | 100 |
| PPV | 100 |
| NPV | 92 |

7.3 Validation of the 13-Gene Signature

By selecting only the 13-gene expression values of the proposed signature from the entire dataset, a discriminant model with 1 component ($R^2=74\%$ and $Q^2=66\%$) was derived. Taking as reference the recurrence status, the signs of the regression coefficients associated to each gene (Table XX) reflected the over- or under-expression pattern in the recurrent states, as detailed in Table I.

TABLE XX

Coefficients of the scaled and centered data of the 13-gene signature PLS-DA model.

| Gene Symbol | Coefficient |
|---|---|
| ACADVL | −0.13 |
| CARHSP1 | −0.20 |
| CCDC144A | −0.14 |
| CNTNAP1 | 0.18 |
| DDX5 | −0.14 |
| DNASE1L2 | −0.19 |
| EHD4 | 0.14 |
| PIP4K2C | 0.17 |
| RNF103 | 0.19 |
| SEZ6L | −0.15 |
| SLC22A6 | 0.16 |
| UGGT2 | 0.15 |
| WDR52 | 0.19 |

Figure 3:
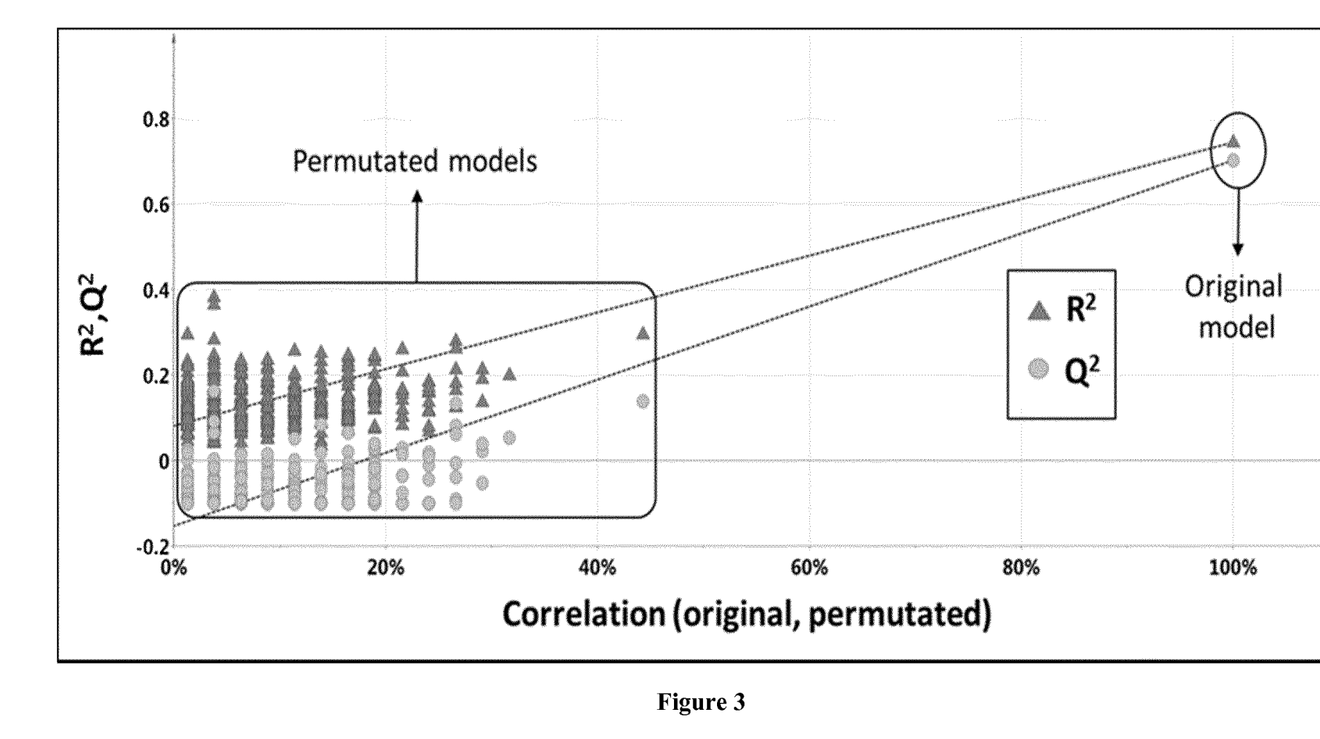
FIG. 3: Perturbation test results for the PLS-DA model of the 13-genes signature. X-axis shows the correlation coefficient (%) between the permutated and the original data. Y-axis is the value of $R^2$ and $Q^2$. The two values on the right hand corner correspond to the values of $R^2$ and $Q^2$ for the original model. Each value on the left side of the plot represents a permutation result. $R^2$ and $Q^2$ values are represented as dark gray triangles and light gray circles, respectively.

A preliminary validation of the 13-gene model was carried out via a Permutation test[5], in order to estimate the degree of overfitting of the model: the class assignment (recurrent and not recurrent) of the patients was randomly permuted 500 times, generating as much models for which $R^2$ and $Q^2$ values were calculated (FIG. 3).

Again, the performances of the permutated models were significantly lower in respect to the original one, excluding the probability of obtain the classification model simply by chance.

According to the evaluation set, the resulting overall accuracy in classification of this 13-gene classifier was 92%, along with the associated statistics as reported in Table XXI.

TABLE XXI 13-gene signature PLS-DA classification statistics.
PPV and NPV statistics are estimated considering a disease (tumor recurrence) prevalence of 33% [9, 10].

|  | Value (%) |
|---|---|
| Sensitivity | 83 |
| Specificity | 100 |
| PPV | 100 |
| NPV | 86 |

7.4 Validation of the 9-Gene Signature

By selecting only the 9 gene expression values of the proposed signature from the entire dataset, a discriminant model with 1 component ($R^2$=64% and $Q^2$=58%) was derived. Taking as reference the recurrence status, the signs of the regression coefficients associated to each gene (Table XXII) reflected the over- or under-expression pattern in the recurrent states, as detailed in Table I.

TABLE XXII

Coefficients of the scaled and centered data of the 9-gene signature PLS-DA model.

| Gene Symbol | Coefficient |
|---|---|
| ACADVL | −0.17 |
| CARHSP1 | −0.25 |
| CNTNAP1 | 0.24 |
| DNASE1L2 | −0.20 |
| RNF103 | 0.14 |
| SEZ6L | −0.22 |
| SLC22A6 | 0.19 |
| UGGT2 | 0.14 |
| WDR52 | 0.20 |

Figure 4:
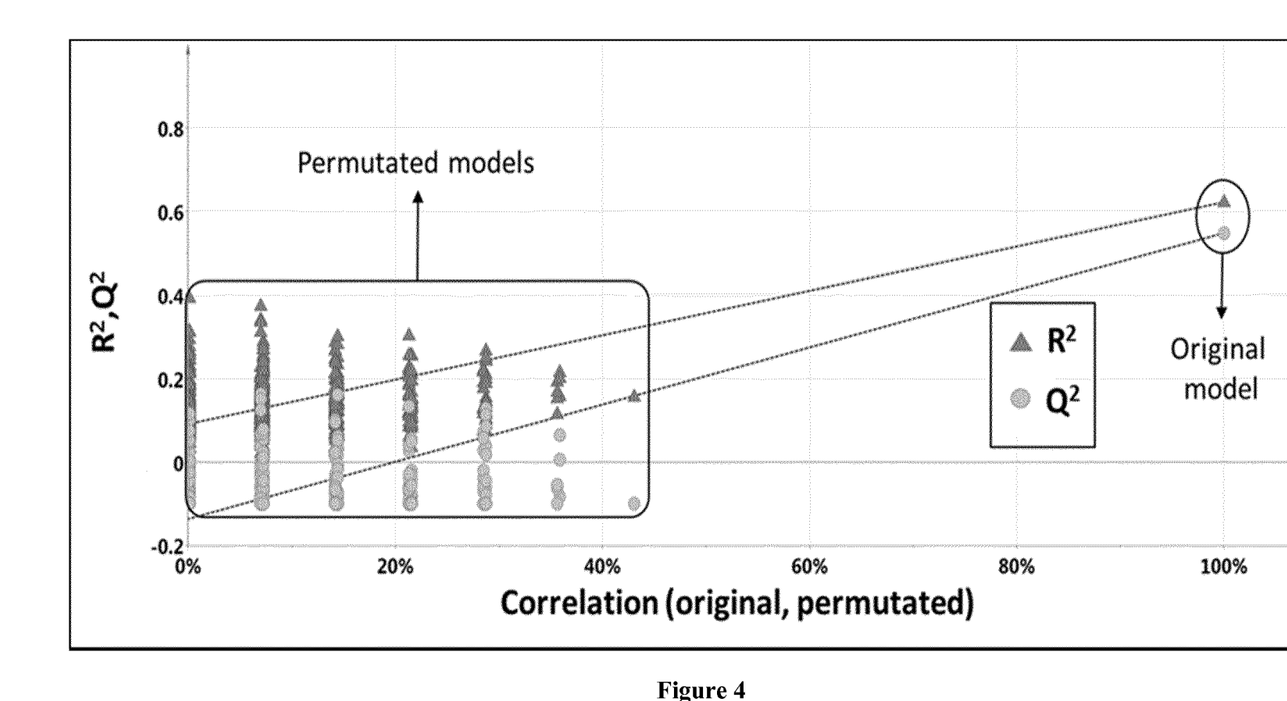
FIG. 4: Perturbation test results for the PLS-DA model of the 9-genes signature. X-axis shows the correlation coefficient (%) between the permutated and the original data. Y-axis is the value of $R^2$ and $Q^2$. The two values on the right hand corner correspond to the values of $R^2$ and $Q^2$ for the original model. Each value on the left side of the plot represents a permutation result. $R^2$ and $Q^2$ values are represented as dark gray triangles and light gray circles, respectively.

A preliminary validation of the 9-gene model was carried out via a Permutation test[5], in order to estimate the degree of overfitting of the model: the class assignment (recurrent and not recurrent) of the patients was randomly permuted 500 times, generating as much models for which $R^2$ and $Q^2$ values were calculated (FIG. 4).

By this calculation it was clear that it was not possible to obtain a model with the same goodness of fit and predictive properties simply by change.

According to the evaluation set, the resulting overall accuracy in classification of this 13-gene classifier was 88%, along with the associated statistics as reported in Table XXIII.

TABLE XXIII 9-gene signature PLS-DA classification statistics.
PPV and NPV statistics are estimated considering a disease (tumor recurrence) prevalence of 33% [9, 10].

|  | Value (%) |
|---|---|
| Sensitivity | 83 |
| Specificity | 92 |
| PPV | 91 |
| NPV | 85 |

LIST OF ABBREVIATIONS

PCa: Prostate Cancer
RP: Radical Prostatectomy
MSKCC: Memorial Sloan Kettering Cancer Center
NCBI: National Center for Biotechnology Information
EST: Expressed sequence tag
St.dev.: Standard Deviation
PLS: Partial Least Square
PLS-DA: Partial Least Square Discriminant Analysis
PPV: Positive Predictive Value
NPV: Negative Predictive Value

REFERENCES

1) Bettuzzi S, Scaltriti M, Caporali A, Brausi M, D'Arca D, Astancolle S, Davalli P, Corti A. Successful prediction of prostate cancer recurrence by gene profiling in combination with clinical data: a 5-year follow-up study. Cancer Res. 2003 Jul. 1; 63(13):3469-72.
2) Komisarof J, McCall M, Newman L, Bshara W, Mohler J L, Morrison C, Land H1. A four gene signature predictive of recurrent prostate cancer. Oncotarget. 2017 Jan. 10; 8(2):3430-3440.
3) Sun Y, Goodison S. Optimizing molecular signatures for predicting prostate cancer recurrence. Prostate 2009 Jul. 1; 69(10):1119-27.
4) Chen X, Xu S, McClelland M, Rahmatpanah F, Sawyers A, Jia Z, et al. An Accurate Prostate Cancer Prognosticator Using a Seven-Gene Signature Plus Gleason Score and Taking Cell Type Heterogeneity into Account. PLoS ONE 2012; 7(9): e45178.
5) Bismar T A, Demichelis F, Riva A, Kim R, Varambally S, He L, Kutok J, Aster J C, Tang J, Kuefer R, Hofer M D, Febbo P G, Chinnaiyan A M, Rubin M A. Defining aggressive prostate cancer using a 12-gene model. Neoplasia 2006; 8:59-68.
6) Glinsky G V1, Glinskii A B, Stephenson A J, Hoffman R M, Gerald W L. Gene expression profiling predicts clinical outcome of prostate cancer. J Clin Invest. 2004 Mar.; 113(6):913-23.
7) Stephenson A J, Smith A, Kattan M W, Satagopan J, Reuter V E, Scardino P T, Gerald W L. Integration of gene expression profiling and clinical variables to predict prostate carcinoma recurrence after radical prostatectomy. Cancer. 2005; 104:290-298.
8) Barrett T, Troup D B, Wilhite S E, Ledoux P, Rudnev D, Evangelista C, Kim I F, Soboleva A, Tomashevsky M, Edgar R. NCBI GEO: mining tens of millions of expression profiles-database and tools update. Nucleic Acids Res. 2007; 35:D760-D765.
9) National Comprehensive Cancer network. Prostate Cancer (version 1, 2015). http//www.nccn.org/patients/guidelines/prostate/.
10) Ward J F, Blute M L, Slezak J, Bergstralh E J, Zincke H. The long-term clinical impact of biochemical recurrence prostate cancer 5 or more years after radical prostatectomy. J Urol. 2013; 170:1872-1876.
11) Wold, S., Sjostrom, M. and Eriksson, L. PLS-Regression: A Basic Tool of Chemometrics. Chemometrics and Intelligent Laboratory Systems. 2001; 58, 109-130.
12) Stephenson A. J. et al., Integration of Gene Expression Profiling and Clinical Variables to Predict Prostate Carcinoma Recurrence after Radical Prostatectomy. Cancer 2005, vol. 104, no. 2: 290-298.

The invention claimed is:

1. An assay device comprising an array consisting of multiple polynucleotide probes complementary and/or hybridizable to the mRNAs of ACADVL, CARHSP1, CNTNAP1, DNASE1L2, RNF103, SEZ6L, SLC22A6, UGGT2, WDR52, and optionally one or more selected from ATP5D, C14orf109, CCDC144A, CDH15, CELSR3, DDX5, EHD4, EPHB3, LOC100508936, PABPC1, PIP4K2C, and PLCG1 genes, wherein the multiple polynucleotide probes are immobilized on a solid support.

2. The assay device according to claim 1, wherein said multiple polynucleotide probes are complementary and/or hybridizable to the mRNAs of ACADVL, CARHSP1, CNTNAP1, DNASE1L2, RNF103, SEZ6L, SLC22A6, UGGT2, and WDR52 genes.

3. The assay device according to claim 1, wherein said multiple polynucleotide probes are consist of sequences complementary and/or hybridizable to the mRNAs of ACADVL, CARHSP1, CCDC144A, CNTNAP1, DDX5, DNASE1L2, EHD4, PIP4K2C, RNF103, SEZ6L, SLC22A6, UGGT2, and WDR52 genes.

4. The assay device according to claim 1, wherein said multiple polynucleotide probes are complementary and/or hybridizable to the mRNAs of ACADVL, C14orf109, CARHSP1, CCDC144A, CDH15, CELSR3, CNTNAP1, DDX5, DNASEIL2, EHD4, PABPC1, PIP4K2C, RNF103, SEZ6L, SLC22A6, UGGT2, and WDR52 genes.

5. The assay device according to claim 1, wherein said multiple polynucleotide probes are complementary and/or hybridizable to the mRNAs of ACADVL, ATP5D, C14orf109, CARHSP1, CCDC144A, CDH15, CELSR3, CNTNAP1, DDX5, DNASE1L2, EHD4, EPHB3, LOC100508936, PABPC1, PIP4K2C, PLCG1, RNF103, SEZ6L, SLC22A6, UGGT2, and WDR52 genes.

6. The assay device according to claim 1, wherein the array is a microarray and the multiple polynucleotide probes are immobilized on a solid glass substrate or membrane in separate locations or spots.

7. A kit containing the assay device according to claim 1 and at least one reagent.

8. The kit according to claim 7, wherein the reagent comprises a labeled primer, a nucleotide, or a combination thereof.

9. The kit according to claim 8, wherein the reagent comprises biotin labeled dNTPs.

10. The kit according to claim 7, further comprising at least one enzyme.

11. The kit according to claim 10, wherein the at least one enzyme comprises a reverse transcriptase.

* * * * *

UNITED STATES PATENT AND TRADEMARK OFFICE
CERTIFICATE OF CORRECTION

PATENT NO. : 12,180,550 B2  
APPLICATION NO. : 17/292748  
DATED : December 31, 2024  
INVENTOR(S) : Andrea Ferraris et al.

Page 1 of 1

It is certified that error appears in the above-identified patent and that said Letters Patent is hereby corrected as shown below:

In the Claims

Claim 3 at Column 28, Lines 25-26, "probes are consist of sequences complementary" should read "probes are complementary"

Claim 4 at Column 28, Line 34, "DNASEIL2" should read "DNASE1L2"

Signed and Sealed this  
Fourth Day of February, 2025

Coke Morgan Stewart  
*Acting Director of the United States Patent and Trademark Office*